United States Patent [19]

Bisagni et al.

[11] 4,434,290
[45] Feb. 28, 1984

[54] PYRIDO (4,3-B) CARBAZOLES SUBSTITUTED IN THE 1 POSITION BY A POLYAMINE CHAIN

[75] Inventors: Emile Bisagni, Orsay; Claire Ducrocq, Les Ulis-Orsay; Christian Rivalle, Villebon; Pièrre Tambourin, Les Ulis-Orsay; Francoise Wendling, Paris; Alain Civier, Montlhery; Luc Montagnier, Le Plessis-Robinson; Jean-Claude Chermann, Elancourt; Jacqueline Gruest, L'Hay-les-Roses; Rosette Lidereau, Colombes, all of France

[73] Assignee: Agence Nationale de Valorisation de la Recherche, Neuilly sur Seine, France

[21] Appl. No.: 259,553

[22] Filed: May 1, 1981

Related U.S. Application Data

[63] Continuation of Ser. No. 75,756, Sep. 14, 1979, abandoned.

[30] Foreign Application Priority Data

Sep. 21, 1978 [FR] France .............................. 78 27137

[51] Int. Cl.³ .......................................... C07D 471/04
[52] U.S. Cl. ........................................ 546/70; 424/258; 424/262
[58] Field of Search ................................. 546/70

[56] References Cited

U.S. PATENT DOCUMENTS 2,477,049 7/1949 Dobson et al. ................. 546/70
3,933,827 1/1976 Brossi et al. .................... 546/70

Primary Examiner—Paul M. Coughlan, Jr.
Assistant Examiner—D. B. Springer
Attorney, Agent, or Firm—Hammond & Littell, Weissenberger and Muserlian

[57] ABSTRACT

The novel derivatives correspond to the general formula:

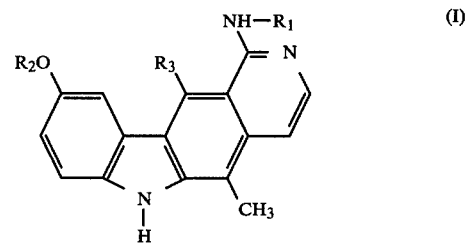

in which $R_1$ is a $Y-(CH_2)_n-NR_4R_5$ group, where Y represents a single bond or the group

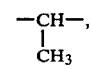

$R_4$ and $R_5$, identical or different, are hydrogen or an alkyl radical, preferably a lower alkyl, or again form together a ring which can include heteroatoms, in particular nitrogen atoms. n is a number ranging from 1 to 10, notably from 2 to 7, $R_2$ is a hydrogen atom, a lower alkyl group or an aralkyl group in which the alkyl substituent is a lower alkyl group, and $R_3$ is a hydrogen atom or a $CH_3$ group useful for the treatment of leukemias.

3 Claims, No Drawings

PYRIDO (4,3-B) CARBAZOLES SUBSTITUTED IN THE 1 POSITION BY A POLYAMINE CHAIN

This application is a continuation of our copending, U.S. patent application Ser. No. 075,756, filed Sept. 14, 1979, now abandoned.

BACKGROUND OF THE INVENTION

1. Field of the Invention

The invention relates to the synthesis of a novel family of products, which are the pyrido[4,3-b]carbazoles (ellipticines) variously substituted at their top 1. The invention also relates to a process for preparing such products from pyrido[4,3-b]carbazoles themselves prepared by a novel route. In addition, the invention relates to the application by way of medicaments of these novel products, in particular for the treatment of leukemias. Thus the invention relates also to pharmaceutical compositions containing, as active agents, at least one of said products.

2. Description of the Prior Art

Numerous studies have been devoted, in the course of recent years, to the family of ellipticine and its derivatives, whose antitumoral activity has been observed. Various processes have been described in the prior art for preparing pyrido[4,3-b]carbazoles (ellipticines). By way of bibliographic reference, may be mentioned, for example, the article of M. SAINSBURY, in Synthesis, 1977, p. 437 et seq. It's still desirable, however, to find new compounds endowed with higher activity or to develop novel routes of synthesis.

GENERAL DESCRIPTION OF THE INVENTION

Accordingly the present invention relates to novel pyrido[4,3-b]carbazoles (ellipticines) substituted at the 1 position by a polyamine chain and corresponding to the general formula (I):

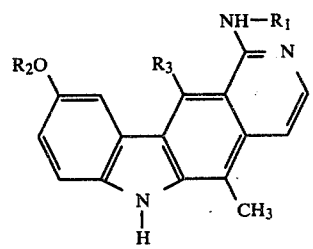

in which $R_1$ is $Y(CH_2)_n$—$N R_4 R_5$ group where Y represents a single bond or the group:

$R_4$ and $R_5$, identical or different, are hydrogen or an alkyl radical, preferably a lower alkyl, or again form together a ring which can include heteroatoms, in particular nitrogen atoms and n is a number ranging from 1 to 10 and notably from 2 to 7, $R_2$ is a hydrogen atom, a lower alkyl group or an aralkyl group in which the alkyl substituent is a lower alkyl group, and $R_3$ is a hydrogen atom or a —$CH_3$ group.

In the sense of the present specification, by "lower alkyl" it means any hydrocarbon group of the formula $C_xH_{2x+1}$ in which x is a whole number ranging from 1 to 4, for example the methyl, ethyl, butyl or propyl radicals.

The invention also relates to the pharmaceutically acceptable salts of the above-defined derivatives, obtained with mineral or organic acids currently used for the formation of pharmaceutically acceptable salts.

The invention also relates to a process for the production of the novel compounds of formula (I), by using 1-chloro-pyrido[4,3-b]carbazoles.

The process of the invention involves a succession of steps which are illustrated by the following reaction diagram:

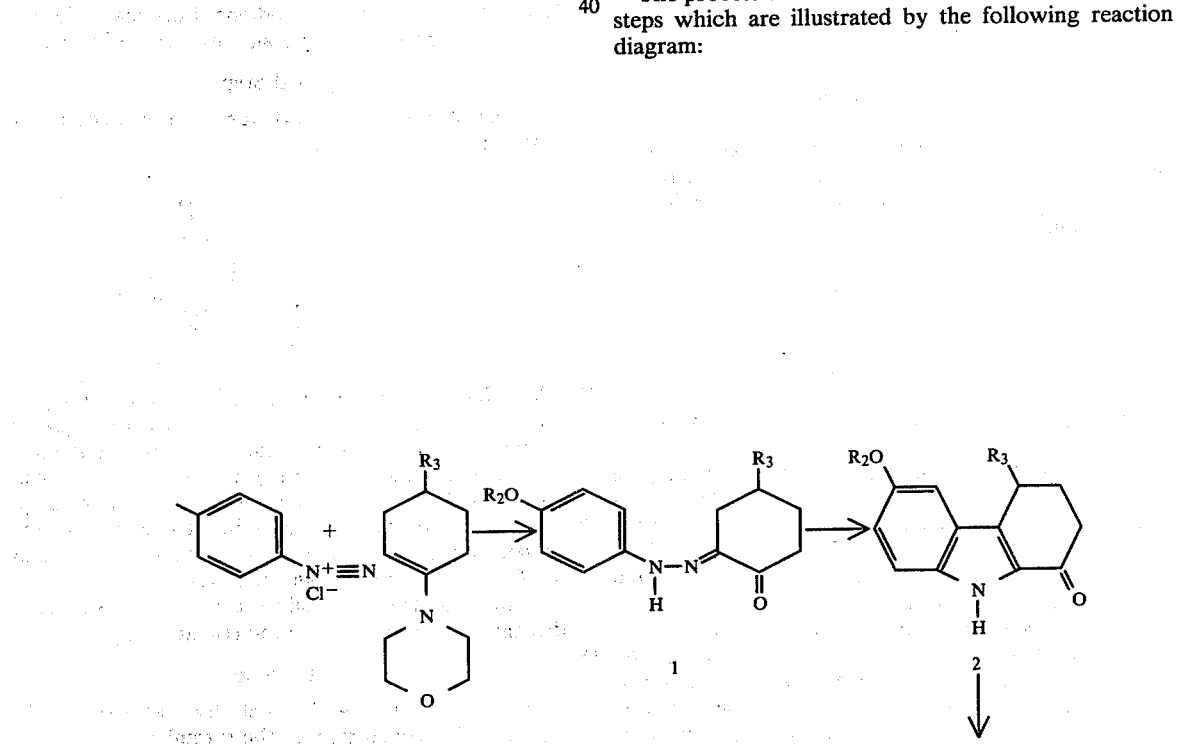

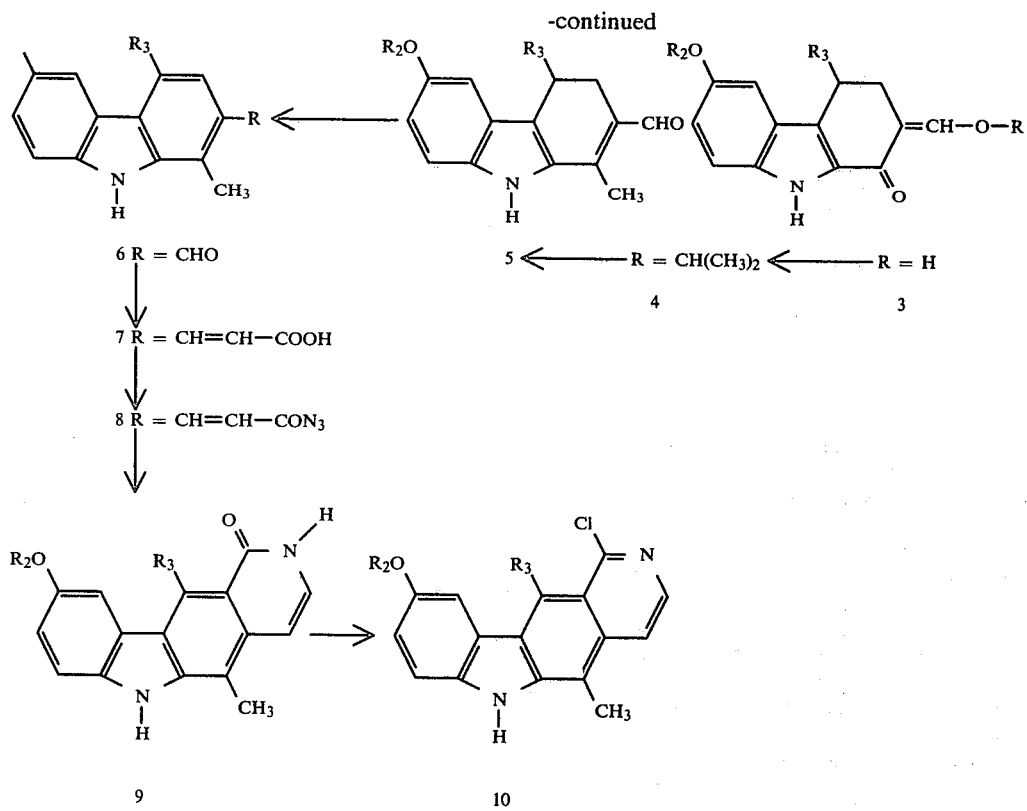

Each of the steps involved are described below.

First Step

In this step, a phenyl diazonium chloride (substituted at the 4 position) of the formula:

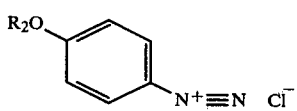

where $R_2$ has the previously indicated meaning is reacted with a cyclohexene having an amine substitution at the 1 position, for example a 1-N-morpholino-cyclohexene of the formula

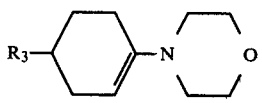

where $R_3$ has the above indicated meaning (H or —$CH_3$).

In view of the reaction, it is advantageous to prepare the diazonium salt in situ by reacting a nitrite, such as sodium nitrite, in an acid medium, with a phenylamine substituted in the 4 position by the —$OR_2$ group. This reaction is effected at a temperature lower than room temperature, for example around 0° C. It is then possible to react the cyclohexene having the amine substitution at the 1 position in the same reaction medium. A 1-N-morpholino-cyclohexene, a 1-N-piperidino-cyclohexene or an other cyclohexene substituted at the 1 position by an amine ring is used. In this way a monoarylhydrazone of a cyclohexane-1,2-dione (formula 1 in the above-mentioned reaction diagram) is thus obtained.

Second Step

In this step, the monoarylhydrazone obtained in the first step, of the formula:

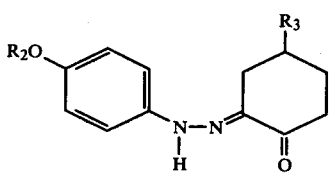

where $R_2$ and $R_3$ have the above indicated meaning, is converted by indolization in the hot and in a strong acid medium. The reaction temperature depends on the medium selected and is generally situated between about 80° C. and 200° C. When operating in a solvent medium, it is possible to work at the reflux temperature of the solvent, for example, in the case of ethanol, at around 80° C., or in the case of water, towards 100° C.

In this way there is obtained a 1-oxo-1,2,3,4-tetrahydro-carbazole (formula 2 in the reaction diagram).

Third Step

In this step, 1-oxo-1,2,3,4-tetrahydro-carbazole obtained in the second step, of the formula:

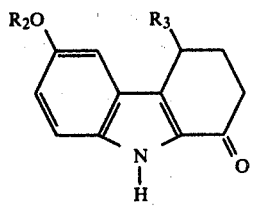

where $R_2$ and $R_3$ have the meaning above indicated, is acylated by means of ethyl-formate in the presence of a strong base, which leads to 1-oxo-2-hydroxymethylene-1,2,3,4-tetrahydro-carbazole (formula 3 in the reaction diagram).

As strong base, it is possible to use sodium hydride, sodium ethoxide or a similar strong base used conventionally in organic chemical reactions. The reaction temperature will depend on the base used. If the temperature is increased, the reaction speed increases.

Fouth Step

In this step, 1-oxo-2-hydroxymethylene-1,2,3,4-tetrahydro-carbazole, of the formula:

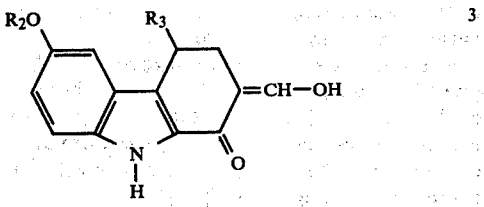

where $R_2$ and $R_3$ have the above indicated meaning, are etherified by means of a suitable alkyl halide, preferably isopropyl iodide. The reaction well works in a basic medium (potassium carbonate, for example) or in an aprotic solvent (dimethyl-formamide, for example). It is possible to start the reaction in the cold, for example towards 0°–5° C., and then to terminate it at room temperature.

In this way a 1-oxo-2-alkyloxymethylene-3,4-dihydro-carbazole is obtained, in particular 1-oxo-2-isopropoxymethylene-3,4-dihydro-carbazole, is obtained (formula 4 in the reaction diagram.

Fifth Step

In this step, 1-oxo-2-isopropoxymethylene-3,4-dihydro-carbazole, obtained in the fourth step, of the formula:

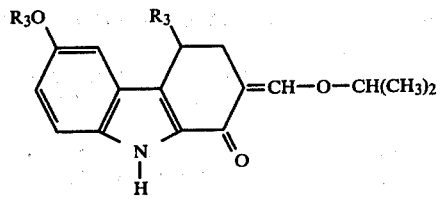

where $R_2$ and $R_3$ have the above indicated meaning, is treated with four molar equivalents of methyl-lithium, after which an acid hydrolysis and an alkaline hydrolysis are successively carried out, the latter being effected at room temperature. The reaction with the methyl-lithium and the acid hydrolysis are best effected in the cold, for example around 0° C. In this way there is obtained a 1-methyl-2-formyl-3,4-dihydro-carbazole (formula 5 in the reaction diagram).

Sixth Step

In this step, 1-methyl-2-formyl-3,4-dihydro-carbazole obtained in the fifth step, of the formula:

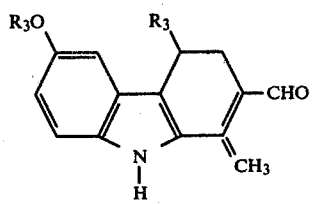

where $R_2$ and $R_3$ have the indicated signification, are treated with palladium charcoal or better with manganese dioxide, in order to obtain aromatization of the starting compound, which leads to the aldehyde of formula 6 (see above reaction diagram).

The reaction works in a solvent medium, for example, a benzene solvent, at a temperature of 70° C. to 120° C. approximately. In the case of benzene, it is possible to operate at reflux temperature, namely about 80° C.

Seventh Step

In this step, the aldehyde obtained in the sixth step, of the formula:

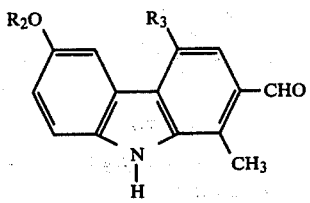

is treated with malonic acid to produce an acrylic acid (formula 7 in the reaction diagram). It is convenient to carry out the reaction in the presence of a catalytic amount of piperidine and in the hot. It is advantageously to operate in boiling pyridine.

Eighth Step

In this step, the acrylic acid obtained in the seventh step, of the formula:

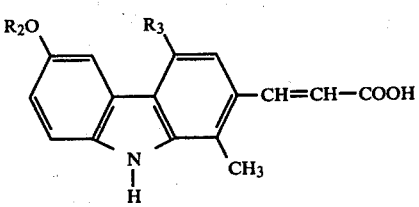

is treated with ethyl chloroformate and then with sodium azide, according to the technique known as mixed anhydrides, which leads to the corresponding azide (formula 8 in the reaction diagram). This reaction works in the cold, in a solvent medium, such as acetone.

Ninth Step

In this step, the azide obtained in the eighth step, of the formula:

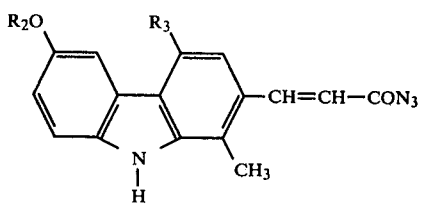

is hot treated with diphenyl-ether, preferably at boiling temperature, which leads to a 1,2-dihydro-1-oxo-5-methylpyrido[4,3-b]carbazole (formula 9 in the reaction diagram).

Tenth Step

In this step, the 1,2-dihydro-1-oxo-5-methyl-pyrido-[4,3-b]carbazole, obtained in the ninth step, of the formula:

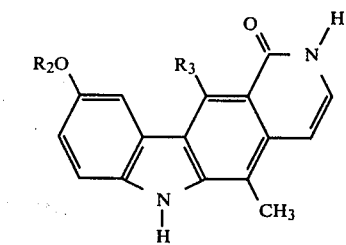

is hot reacted with phosphorus oxychloride, and preferably at boiling temperature, which leads to 1-chloro 5-methyl-9-alkyloxy-pyrido[4,3-b]carbazole (formula 10 in the reaction diagram).

Eleventh Step

In this step, 1-chloro-5-methyl-9-alkyloxy-pyrido[4,3-b]carbazole obtained in the tenth step, of the formula:

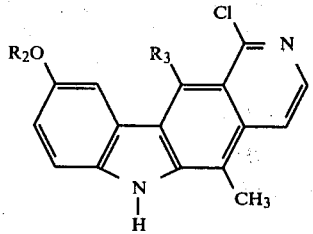

is reacted with an amine of the formula $NH_2-R_1$, where $R_1$, $R_2$ and $R_3$ have the previously indicated meaning. Substitution by the amine is advantageously done in the hot, notably at temperatures of 100° to 200° C., and in particular in the amine at reflux. The invention also relates to the carbazoles of formula 10 per se as new compounds. The pharmaceutically acceptable salts of said derivatives of the invention may be obtained by conventional means within the scope of the one skilled in the art using suitable acids, such as hydrochloric, hydrobromic, succinic, lactic, acetic, maleic, phosphoric acids and any other acids commonly used to form such salts.

The carbazoles with an aldehyde function of formula 6 in the above reaction diagram are products valuable for organic synthesis. For example, they can be applied to the preparation of various derivatives of ellipticine by the technique described by T. R. Govindachari, S. Rajappa, V. Sundarasanam, Indian Journal of Chemistry 1 p. 247(1963). In addition, they can serve for the production of olivacine derivatives by the technique described by E. Wenkert and K. G. Dave J. Am. Chem. Soc. (1962) 84, p. 94.

The invention also relates to such carbazoles of the formula:

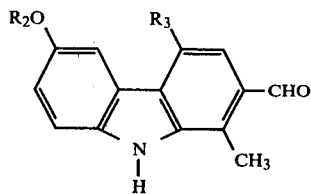

where $R_2$ is a hydrogen atom, a lower alkyl group or an aralkyl group in which the alkyl substituent is a lower alkyl group, and $R_3$ is a hydrogen atom or a $CH_3$ group.

Representative examples of these carbazoles are given below (Example 6, compounds 6a, 6b with $R_3=H$ and 6c, 6d with $R_3=CH_3$).

The following examples illustrate, by means of a certain number of representative compounds, the synthesis according to the invention. With reference to the above reaction diagram, the reaction scheme used in the various examples will first be indicated.

The 4-methoxy phenyl-diazonium and 4-benzyloxy-phenyldiazonium react at 0° C. with 1-N-morpholino-cyclohexene and 4-methyl-1-N-morpholino cyclohexene giving respectively the monoarylhydrazones of cyclohexane-1,2-dione and 4-methyl-cyclohexane-1,2-dione (compounds 1a, 1b, 1c, 1d).

Starting from these arylhydrazones 1 (a–d), successively there are prepared:

the 1-oxo-1,2,3,4-tetrahydro-6-alkyloxy-carbazoles 2 (a–d) which result from the conversion of the preceeding compounds by indolization according to Fisher by the technique described by F. LIONS J. Proc. Roy. Soc. N. S. Wales 66, p. 516 (1933), the 1-oxo-2-hydroxymethylene-1,2,3,4-tetrahydro-6-alkyloxy-carbazoles 3 obtained by acylation of 2 with ethyl formate in the presence of sodium hydride, by the technique described by E. WENKERT and K. G. DAVE J. Am. Chem. Soc. (1962), 84, p. 94, the 1-oxo-2-isopropyloxymethylene-1,2,3,4-tetrahydro-6-alkyloxy-carbazoles 4 formed by etherifying 3 with isopropyl iodide in the presence of potassium carbonate in dimethylformamide by a technique similar to that described by Wenkert and Dave (cited above), the 1-methyl-2-formyl-3,4-dihydro-6-alkyloxy-carbazoles 5 derived from the transformation of 4 by four molar equivalents of methyl-lithium followed by hydrolysis in an acid medium, the 1-methyl-2-formyl-6-alkyloxy-carbazoles 6 arising from the aromatization of 5 by means of manganese dioxide.

From aldehydes 6, the edification of the ring D of the pyrido[4,3-b]carbazoles was effected in three steps, under the reaction conditions described by E. ELOY and A. DERYCKERE Helv. Chem. Acta. (1969), 52, p. 1755. Thus, malonic acid reacts with 6 (a–d) to give acrylic acids 7 (a–d) which are converted into corresponding azides 8 (a–d) by the mixed anhydride method (11) and, in boiling diphenyl ether (10), the latter generate the 1,2-dihydro-1-oxo-pyrido[4,3-b]carbazoles 9 (a–d) which lead easily to the 1-chloro-5-methyl-9- alkyloxy-pyrido[4,3-b]carbazoles 10 (a–d) by reaction with boiling phosphorus oxychloride.

The 1-chloro-5-methyl-9-alkoxy-pyrido[4,3-b]carbazoles 10 (a–d) are substituted by primary or secondary amines to give rise to expected derivatives 11 to 28.

The two benzyloxylated derivatives 10b and 10d have been synthesized for the comparative study of the biological effects of the methoxylated and hydroxylated derivatives. In fact, by hydrogenation of their substitution derivatives 24 and 28 on palladium charcoal, they have been quantitatively debenzylated into 29 and 30 compounds.

In tables I below are gathered the indications relating to the signification of $R_1$, $R_2$ and $R_3$ in the compounds of the examples.

a Varian XL 100 apparatus, using tetramethylsilane as internal reference and in solution in $(CD_3)_2SO$.

The compounds marked with the index a correspond to $R_2=CH_3$ and $R_3=H$. The compounds marked with the index b correspond to $R_2=CH_2-\phi$ and $R_3=H$. The compounds marked with the index c correspond to $R_2=R_3=CH_3$. The compounds marked with index d correspond to $R_2=CH_2-\phi$ and $R_3=CH_3$.

DESCRIPTION OF PREFERRED EMBODIMENTS

EXAMPLE 1

(4-methoxy-phenyl)hydrazones: compounds 1a and 1c p. anisidine (123 g—1 mole) was mixed with concentrated hydrochloric acid (172 ml—2 moles), and it was stirred until complete solution of the p. anisidine and 400 g of ice was added. Keeping the temperature of the mixture below 5° C. and continuing stirring, there was then added, drop by drop, a solution of sodium nitrite (60 g—1 mole) in the minimum of water. Continuing to stir the whole below 3° C., the desired enamine was then added (1 mole), corresponding respectively to $R_2=CH_3$ and $R_3=H$ for the compound 1a and $R_2=CH_3$ and $R_3=CH_3$ for the compound 1b, in solution in dried and diperoxidized dioxane (400 ml); the stirring was continued for 1 hour allowing it to come

TABLE I

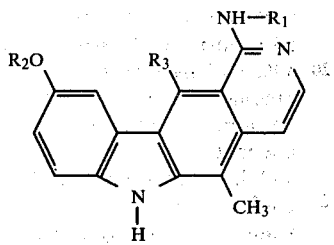

| | | | | |
|---|---|---|---|---|
| 10a → | 11 | $R_2 = CH_3$; | $R_3 = H$ | $R_1 = (CH_2)_2-NH_2$ |
| | 12 | " | " | $R_1 = (CH_2)_3-NH_2$ |
| | 13 | " | " | $R_1 = (CH_2)_4-NH_2$ |
| | 14 | " | " | $R_1 = (CH_2)_5-NH_2$ |
| | 15 | " | " | $R_1 = (CH_2)_6-NH_2$ |
| | 16 | " | " | $R_1 = (CH_2)_2-N(CH_3)_2$ |
| | 17 | " | " | $R_1 = (CH_2)_3-N(CH_3)_2$ |
| | 18 | " | " | $R_1 = (CH_2)_3-N(C_2H_5)_2$ |
| | 19 | " | " | $R_1 = -CH(CH_3)-(CH_2)_3-N(C_2H_5)_2$ |
| | 20 | $R_2 = CH_3$; | $R_3 = H$ | $R_1 = -(CH_2)_3-N[\text{piperazine}]-N-(CH_2)_3-NH_2$ |
| | 21 | " | " | $R_1 = N[\text{piperidine}]$ |
| 10b → | 22 | $R_2 = CH_2C_6H_5$; | $R_3 = H$ | $R_1 = (CH_2)_2-N(CH_3)_2$ |
| | 23 | " | " | $R_1 = (CH_2)_3-NH_2$ |
| | 24 | " | " | $R_1 = (CH_2)_3-N(C_2H_5)_2$ |
| 10c → | 25 | $R_2 = R_3 = CH_3$ | | $R_1 = (CH_2)_3-NH_2$ |
| | 26 | " | | $R_1 = (CH_2)_3-N(CH_3)_2$ |
| | 27 | " | | $R_1 = (CH_2)_3-N(C_2H_5)_2$ |
| 10d → | 28 | $R_2 = CH_2C_6H_5$; | $R_3 = CH_3$ | $R_1 = (CH_2)_3-N(C_2H_5)_2$ |
| 24 → | 29 | $R_2 = R_3 = H$ | | $R_1 = (CH_2)_3-N(C_2H_5)_2$ |
| 28 → | 30 | $R_2 = H$; | $R_3 = CH_3$ | $R_1 = (CH_2)_3-N(C_2H_5)_2$ |

It will be noted that the compound 21 does not enter into the general definition of the products of the invention. Pharmacological tests have also shown that this compound is not cytotoxic.

In the Examples which follow, the melting points, uncorrected, have been taken on a Kofler heating bench or with a heating plate microscope. The IR spectra were recorded on a Perkin Elmer double-beam spectrophotometer, modele 21. Except for indications to the contrary, the NMR spectra were recorded with Hitachi-Perkin Elmer apparatus at 60 MHz, the others with back to room temperature, the precipitate was filtered off and washed with water and then with ethanol. The red solid obtained was taken up again in 1 l of boiling ethanol and, after cooling, it was filtered off and dried to give brick red crystals.

(4-benzyloxy-phenyl)hydrazones: compounds 1b and 1d

Finely powdered 4-benzyloxy-aniline hydrochloride (235.5 g—1 mole) was suspended in 500 ml of N-hydrochloric acid; the resulting mixture was cooled to 0° C., then treated successively with sodium nitrite and the desired enamine (1-N-morpholino cyclohexene or 4-methyl 1-N-morpholino cyclohexene) under the same conditions as for forming 1a and 1b.

The characteristics of the compounds 1a, 1b, 1c and 1d are given in Table II.

TABLE II

Compounds 1a - 1b - 1c - 1d

| | M.P. °C. (a) | Yield % | | C | Analysis c: calculated % f: found % H | N |
|---|---|---|---|---|---|---|
| 1a* | 204-5 dec. | 85 | c f | 67.22 67.28 | 6.94 6.82 | 12.06 12.02 |
| 1b | 161-2 | 76 | c f | 74.00 73.70 | 6.54 6.32 | 9.09 9.21 |
| 1c | 159-60 dec. | 77 | c f | 68.27 68.57 | 7.37 7.23 | 11.37 11.58 |
| 1d | 165 | 82 | c f | 74.51 74.38 | 6.88 6.65 | 8.69 8.74 |

*: Compound already described by V. I. Shvedov, L. B. Altukhova and A. N. Grinev Chemical Abstracts (1965) 63, p. 6893 h.
(a): Analytical Samples recrystallized from ethanol.
IR: $\nu$ NH: 3220 to 3240, $\nu$ C = O: 1660 to 1665, $\nu$ N = C: 1490 to 1495, 1515 to 1520 cm$^{-1}$.

EXAMPLE 2

1-oxo-1,2,3,4-tetrahydro-6-alkyloxy-carbazoles: compounds 2a, 2b, 2c and 2d

Pure sulphuric acid, d=1.84 (196 g, 2 moles), is added to absolute ethanol (2.5 l). Keeping the resulting hot solution under stirring, there was then added in a single amount one of the hydrazones obtained in Example 1 (1 mole). The whole is heated under reflux for 2 to 4 hours, that is to say until complete disappearance of the stain corresponding to the starting compound on a silica gel plate, and it was allowed to cool. The precipitate formed was filtered off and the mother liquors, concentrated to 800 ml and made up to 2 l with water, were left with stirring overnight to give a small additional fraction of the expected ketone, besides a black viscous oil. The whole of the solid was washed with ethanol and then recrystallized from the solvent indicated in Table III, which shows also the characteristics of the products obtained.

TABLE III

Compounds 2a - 2b - 2c - 2d

| M.P. °C. | Yield % | Solvent of recrystallization | | C | Analysis c: calculated % f: found % H | N |
|---|---|---|---|---|---|---|
| 2a* | 216-19 | 60 | Ethanol | c f | 72.54 72.34 | 6.09 6.22 | 6.51 6.51 |
| 2b | 211 | 40 | Dimethyl formanide | c f | 78.33 78.05 | 5.88 5.93 | 4.81 4.76 |
| 2c | 133-4 bp/0.15 = 214-40 | 30 | Ethanol | c f | 73.34 73.49 | 6.60 6.56 | 6.11 6.24 |
| 2d | 193 | 50 | Xylene | c f | 78.66 78.88 | 6.27 6.29 | 4.59 4.35 |

*: Compound already described by B. Douglas, J. L. Kirpatrick, B. P. Moore and J. A. Weisbach, Australian Journal of Chemistry (1964) 17, 246.

EXAMPLE 3

1-oxo-2-hydroxymethylene-1,2,3,4-tetrahydro-6-alkyloxy carbazoles: compounds 3a, 3b, 3c and 3d In a triple necked flask of 4 l provided with a refrigerating system and a stirring system, was introduced one of the compounds 2 obtained in Example 2 (1 mole) and ethyl formate (1300 ml—large excess), then gradually 50% sodium hydride in oil (48 g—2 moles) was added gradually. An exothermic reaction occured which brought the ethyl formate to reflux and, after 30 minutes under stirring, 48 g of sodium hydride was again added and the reaction continued for a further 30 minutes. The cooled reaction mixture was poured into 2.5 l of iced water; the resulting mixture was acidified with hydrochloric acid, The precipitate formed was filtered, washed with water, dried and recrystallized from the solvent indicated in Table IV to give yellow crystals. The characteristics of the products 3 are indicated in Table IV.

TABLE IV

Compounds 3a - 3b - 3c - 3d

| | M.P. °C. | Yield % | Solvent of recrystallization | | C | Analysis c: calculated f: found % H | N |
|---|---|---|---|---|---|---|---|
| 3a | 165-170 | 85 | Methanol/ water 60/40 v/v | c f | 69.16 69.39 | 5.39 5.46 | 5.76 5.48 |
| 3b | 190 | 95 | acetic acid | c f | 75.22 75.50 | 5.37 5.50 | 4.38 4.12 |
| 3c | 175-7 | 86 | Benzene | c f | 70.00 70.13 | 5.88 5.70 | 5.44 5.29 |
| 3d | 178-82 dec. | 77.5 | Xylene | c f | 75.65 75.82 | 5.74 5.96 | 4.20 3.92 |

IR: $\nu$ OH: 3200 to 3280, $\delta$ OH: 1110, $\nu$ C = O: 1625 to 1635, $\nu$ C = CHOH: 1565 to 1586, $\nu$ C—O: 1250 to 1275 and 1325 to 1335 cm$^{-1}$.

EXAMPLE 4

1-oxo-isopropyloxy-2-methylene-1,2,3,4-tetrahydro-6-alkyloxy carbazoles: Compounds 4a, 4b, 4c and 4d In a triple necked flask of 4 l was introduced one of the hydroxymethylene derivatives obtained in Example 3 (1 mole); freshly rectified dimethylformamide (960 ml) and dry potassium carbonate (498 g—3.5 moles). To this mixture kept under stirring and cooled below 5° C. with an ice bath, was gradually added isopropyl iodide (840 g—5 moles). At the end of the addition, stirring was continued at around 0° C. for 6 hours and it was finally left to come back to room temperature. The precipitate was filtered off, washed with acetone and the filtrate was evaporated. The residue from the evaporation and the filtered solid were taken up again separately in water, the precipitates formed were filtered off and combined to be recrystallized from the solvent indicated in Table V. The expected isopropyl ethers were produced in the form of yellow flakes or needles. Their characteristics are indicated in Table V.

TABLE V

Isopropyl ethers 4a - 4b - 4c and 4d

| | M.P. °C. | Yield % | Solvent of recrystal- lization | | Analysis c: calculated % f: found % | | |
|---|---|---|---|---|---|---|---|
| | | | | | C | H | N |
| 4a | 187–95 | 84 | Ethanol | c | 71.56 | 6.71 | 4.91 |
| | | | | f | 71.75 | 6.94 | 4.75 |
| 4b | 198 | 60 | Xylene | c | 76.43 | 6.41 | 3.88 |
| | | | | f | 76.14 | 6.62 | 3.97 |
| 4c | 167 | 67 | Methanol or cy- clohexane | c | 72.20 | 7.07 | 4.68 |
| | | | | f | 71.96 | 6.88 | 4.67 |
| 4d | 146–55 | 60 | cyclo- hexane | c | 76.72 | 6.71 | 3.73 |
| | | | | f | 76.95 | 6.72 | 3.41 |

IR: $\nu$ C = O: 1650 to 1655, $\nu$ CH—O: 1570 to 1580 cm$^{-1}$ NMR:DMSO d6: 1.25 to 1.4 d (CH$_3$, J CH$_3$—CH = 6 Hz); 2.1 to 2.4 massive (CH); 4.3 to 4.45 multiplet (CH, J = 6 Hz).

EXAMPLE 5

1-methyl-2-formyl-3,4-dihydro-6-alkyloxy carbazoles: compounds 5a, 5b, 5c and 5d One of the isopropyl ethers obtained in Example 4 (0.175 mole) placed in a triple necked flask of 2 l protected from moisture was dissolved in anhydrous ether (600 ml). To this mixture cooled by an ice bath and kept under stirring, was gradually added methyl-lithium (538 ml of an ether solution assayed to 1.3 M, namely 0.7 mole). The deep red color observed at the beginning disappears towards the end of the addition and, after 30 additional minutes of stirring, the reaction mixture was poured into a saturated ammonium chloride solution (2 l). The resulting mixture was extracted several times with ether and combined organic layers were stirred for 15 minutes in the presence of 200 ml of 6 N hydrochloric acid, which causes the formation of a brown-black precipitate. Then a solution of sodium hydroxide was added until it gave an alkaline pH, the precipitate was redissolved to a great extent and the whole was extracted with ether or with chloroform, until exhaustion. The whole of the organic layer was washed with a solution of N sodium hydroxide, then with water. After drying over potassium carbonate, the solvent was evaporated to give a solid residue. In the case of the derivatives 5a, 5b, and 5c, this solid was taken up in the minimum of benzene, filtered off, then recrystallized from the solvent indicated in Table VI.

With regard to the derivative 5d, it was purified by chromatography on a silica gel column, with methylene chloride as eluting solvent and by following the development of the chromatography on plates. After evaporation of the fractions containing the almost pure aldehyde expected, the residue was recrystallized. The compounds 5 were produced in the form of yellow crystals. Their characteristics are indicated in Table VI.

EXAMPLE 6

1-methyl-2-formyl 6-alkyloxy carbazoles: compounds 6a, 6b, 6c, 6d

In a triple necked flask of 4 l provided with a mechanical stirring device and with a refrigerant, one of the dihydro carbazoles 5 obtained in Example 5 was introduced (0.1 mole), with dry benzene (2 l) and it was heated to boiling to homogenization. There was then added, in a single amount, activated manganese dioxide (15) (110 g—1.26 mole), and it was heated under reflux for 30 minutes maintaining the stirring and then filtered under a hood. The manganese dioxide was washed until exhaustion (acetone or chloroform as the case may be, if necessary hot). The whole of the filtrate was evaporated to dryness and the residue was recrystallized to give yellow needles or prisms. The characteristics of the compounds 6 are indicated in Table VII.

EXAMPLE 7

Trans-$\beta$[2(2-methyl-6-alkyloxy-carbazolyl]-acrylic acids: compounds 7a-7b-7c and 7d One of the aldehydes 6 obtained in the Example 6 is dissolved in dry pyridine (800 ml) containing piperidine (3 ml) and the whole was heated to reflux. To this mixture, was added malonic acid (22.9 g—0.22 mole), the heating was continued to reflux for 15 minutes and this treatment with malonic acid was repeated again twice, the total added being therefore 0.66 mole. After evaporation of the solvent, the solid residue was taken up again in water, filtered off, washed with water and with acetone, dried and recrystallized or simply "digested" in acetic acid to

TABLE VI 1-methyl-2-formyl-3,4-dihydro-6-alkyloxy-carbazoles 5a - 5b - 5c - 5d

| | M.P. °C. | Yield % | Solvent of recrystal- lization | RMN/DMSO d6 | | | | | Analysis c: calculated % f: found % | | |
|---|---|---|---|---|---|---|---|---|---|---|---|
| | | | | CH$_3$-1 | CHO-2 | CH$_3$-4 | NH-9 | | C | H | N |
| 5a | 194 | 80 | xylene | 2.5 | 10.6 | — | 8.6 | c | 74.66 | 6.27 | 5.81 |
| | | | | | | | | f | 74.72 | 6.18 | 5.85 |
| 5b | 158 | 76 | benzene | 2.55 | 10.15 | — | 11.3 | c | 80.89 | 6.17 | 3.93 |
| | | | | | | | | f | 80.85 | 6.49 | 3.97 |
| 5c | 208 | 86 | xylene | 2.5 | 10.5 | d 1.25 J = 6.5Hz | 8.4 | c | 75.27 | 6.71 | 5.49 |
| | | | | | | | | f | 75.58 | 6.79 | 5.29 |
| 5d | 78–80 | 96.5 | benzene | 2.45 | 10.6 | d 1.2 J = 6.5Hz | 8.7 | c | 81.08≠ | 6.48 | 3.78 |
| | | | | | | | | f | 80.90 | 6.33 | 3.51 |

≠calculated for C$_{21}$H$_{19}$NO$_2$, ½ C$_6$H$_6$
IR: $\nu$ C = O: 1605 to 1620 cm$^{-1}$

TABLEAU VII 1-methyl-2-formyl-6-alkyloxy carbazoles 6a - 6b - 6c - 6d

| | M.P. °C. | Yield % | Solvent of recrystallization | RMN/DMSO d6 | | | | Analysis c: calculated % f: found % | | | |
|---|---|---|---|---|---|---|---|---|---|---|---|
| | | | | $CH_3$-1 | CHO-2 | $CH_3$-4 | NH-9 | | C | H | N |
| 6a | 174 | 70 | Ethanol or benzene | 2.9 | 10.4 | — | 11.3 | c | 75.30 | 5.40 | 5.85 |
| | | | | | | | | f | 75.37 | 5.65 | 5.96 |
| 6b | 205 | 73 | Xylene | 2.9 | 10.5 | — | 11.5 | c | 79.88 | 4.99 | 4.44 |
| | | | | | | | | f | 79.92 | 5.32 | 4.71 |
| 6c | | 88 | benzene/cyclohexane 1/1 v/v | 2.8 | 10.45 | 2.8 | 10.15 | c | | | |
| | | | | | | | | f | | | |
| 6d | 162-4 | 50 | xylene | 2.85 | 10.8 | 2.8 | 11.8 | c | 81.67≠ | 6.28 | 3.66 |
| | | | | | | | | f | 81.65 | 6.03 | 3.55 |

IR: $\nu$ C = O: 1650 to 1675 cm$^{-1}$
≠calculated for $C_{22}H_{19}NO_2$, ½ $C_8H_{10}$ give yellow microcrystals. The characteristics of the compounds 7 are indicated in Table VIII.

TABLE VIII

Acrylic acids 7a - 7b - 7c - 7d

| | M.P. °C. | Yield % | RMN/DMSO d6 CH=CH COOH (J = 16Hz) | Analysis c: calculated % f: found % | | |
|---|---|---|---|---|---|---|
| | | | | C | H | N |
| 7a | 293-5 dec | 90 | 6.5-8.15 | c 70.33 f 70.43 | 5.56 5.31 | 4.83$^a$ 4.82 |
| 7b | 265-6 | 88.5 | 6.55-8.2 | c 77.29 f 77.26 | 5.36 5.07 | 3.92 3.83 |
| 7c | 288-98 dec | 66 | 6.6-8.15 | c 73.20 f 72.88 | 5.80 5.78 | 4.74 4.34 |
| 7d | 258-64 dec | 75 | 6.5-8.1 | c 77.6 f 77.37 | 5.70 5.50 | 3.77 3.49 |

$^a$Analysis calculated for $C_{17}H_{15}NO_3$, ½ $H_2O$
IR: $\nu$ OH: 3400, wide band from 2200 to 3200; $\nu$ C = O: 1660 to 1665; $\delta$ OH: 930 to 940 cm$^{-1}$.

EXAMPLE 8

Trans β[2-(2-methyl-6-alkyloxy-carbazolyl)]acrylazides: compounds 8a-8b-8c-8d

The mixture constituted by one of the acrylic acids 7 obtained in Example 7 (0.1 mole), triethylamine (11.1 g—0.11 mole) and acetone (260 ml) was cooled to 0° C. in a bath of ice and salt. Ethyl chloroformate (14.75 g—0.136 mole) in solution in acetone (90 ml) was then added drop by drop with stirring and at 0° C., and 1 hour after the end of the addition, the heterogeneous mixture resulting kept at 0° C. was reacted with sodium azide (9.75 g—0.15 mole dissolved in a minimum of water), itself added drop by drop at 0° C. An hour after the end of the addition, the refrigerating bath was removed, and when the mixture had come back to room temperature, it was poured into water, filtered off, washed with water, then with a little acetone. After drying, the azides thus-formed were in the form of microcrystals which were used in the following reaction without other purification.

EXAMPLE 9

1,2-dihydro-1-oxo-5-methyl-9-alkyloxy (6H) pyrido[4,3-b]carbazoles: compounds 9a-9b-9c and 9d In a triple necked flask provided with a dropping funnel, a dip thermometer and a mechanical stirrer, was introduced diphenyl-ether (180 ml) and tributylamine (4.1 g—22 mMoles). To this mixture heated to 240° C. and kept constantly at this temperature, was added gradually with vigorous stirring one of the azides 8 obtained in Example 8 (20 mMoles), dispersed in diphenyl-ether heated to 50° C. (50 ml). At the end of the addition, the whole was kept at 240°-250° C. for 20 minutes, about half the diphenyl-ether was distilled off under reduced pressure and the solid formed after cooling and the addition of benzene (100 ml) was filtered off. The pyrido[4,3-b]carbazoles 9 are then recrystallized the solvent indicated in Table IX. However, in the case of 9a, the purification was facilitated by prior treatment with a boiling solution of N potassium hydroxide which enabled a small amount of the acid 7a to be removed. The presence of the latter was explained by the low solubility which, under the experimental conditions used, is the cause of its incomplete conversion into the corresponding azide 8a. The characteristics of the products 9 are indicated in Table IX.

EXAMPLE 10

1-chloro-5-methyl-(6H)-9-alkyloxy-pyrido[4,3-b]carbazoles: compounds 10a, 10b, 10c, and 10d One of the 1,2-dihydro-1-oxo-5-methyl-pyrido[4,3-b]carbazoles 9 obtained in Example 9 (20 mmoles), was suspended in phosphorus oxychloride (1 l) and the whole was heated to reflux, with stirring. Generally, there was solution, precipitation of a solid and finally resolution of the latter. After the reflux time indicated in Table 10, the excess oxychloride was removed under reduced pressure and the residual solid was taken up again in water, in the presence of chloroform.

To this mixture kept under stirring at room temperature, was added a solution of N caustic soda until an alkaline pH and it was stirred until the disappearance of the red color and the persistance of a yellow color. The precipitate was filtered off, the chloroform phase was evaporated, the residue was added to the precipitate and the whole was recrystallized from the solvent indicated in Table X. The latter also gathers the characteristics of the compounds 10.

TABLE IX 1,2-dihydro-1-oxo-5-methyl-9-alkyloxy (6H) pyrido [4,3-b] carbazoles 9a - 9b - 9c - 9d

| | M.P. °C. | Yield % | Solvent of recrystal- lization | RMN/DMSO d6 | | | | Analysis c: calculated % f: found % | | |
|---|---|---|---|---|---|---|---|---|---|---|
| | | | | NH-2 | CH$_3$-5 | NH-9 | CH$_3$-11 | C | H | N |
| 9a | 297–302 | 47 | acetic acid | 11.2 | 2.7 | 11.45 | — | c 73.36 f 73.54 | 5.07 5.06 | 10.02 9.96 |
| 9b | 258 | 72 | dioxane | 11.2 | 2.7 | 11.5 | — | c 74.17≠ f 74.32 | 5.41 5.56 | 7.52 7.39 |
| 9c | 292–8 | 59 | dioxane | 11.15 | 2.6 | 11.6 | 3.5 | c 73.95 f 73.55 | 5.52 5.51 | 9.58 9.22 |
| 9d | 268–70 | 30 | dioxane | 10.6 | 2.6 | 11.1 | 2.6 | c 76.37≠≠ f 76.67 | 5.61 5.58 | 7.42 7.45 |

IR: ν NH and OH: 2800–3350; ν C = O: 1635 to 1650 cm$^{-1}$
≠calculated for C$_{23}$H$_{18}$N$_2$O$_2$, H$_2$O
≠≠calculated for C$_{24}$H$_{20}$N$_2$O$_2$, ½ H$_2$O

TABLE X 1-chloro-5-methyl-9-alkyloxy pyrido [4,3-b] carbazoles 10a - 10b - 10c - 10d

| | M.P. °C. | Yield % | Solvent of recrystal- lization | Analysis c: calculated % f: found % | | | |
|---|---|---|---|---|---|---|---|
| | | | | C | H | N | Cl |
| 10a | 264 | 73 | ethyl acetate | c 68.80 f 68.52 | 4.38 4.40 | 9.44 9.25 | 11.97 11.84 |
| 10b | 248–50 | 88 | ethanol then xylene | c 72.82≠ f 72.70 | 5.05 4.82 | 7.08 6.96 | 8.97 9.11 |
| 10c | 241–5 | 25 | xylene | c 69.56 f 69.80 | 4.83 5.07 | 9.02 9.28 | 11.43 11.68 |
| 10d | 221–2 | 70 | xylene | c 74.51 f 74.67 | 4.91 5.12 | 7.24 7.32 | 9.18 9.02 |

≠Calculated for C$_{23}$H$_{17}$ClN$_2$O, ½ C$_2$H$_5$OH

EXAMPLES 11 to 28

1-amino-alkylamino-5-methyl-9-alkyloxy-pyrido[4,3-b]carbazoles: compounds 11 to 28

To one of the chlorinated compounds 10 obtained in Example 10 (500 mg), was added 8 ml or 8 g of the desired amine of the formula NH$_2$—R$_1$ and this mixture was heated to the temperature and for the time indicated in Table XI. After evaporation of the amine excess under vacuum varying from 15 to 0.5 mm of Hg as the case may be, the residue is taken up again in 100 ml of a 0.5 N sodium hydroxide solution and the solid obtained is filtered off, dried and then recrystallized. The conditions of the reaction and the characteristics of the compounds of the invention are indicated in Table IX.

The bimaleate of the compound 27 was prepared according to the following method: the compound 27 was dissolved in alcohol. Separately two equi molar amounts of maleic acid was dissolved in alcohol with an excess of 10%. The two solutions were mixed. Some moments later it was brought to boiling and then allowed to cool. The compound obtained, that is to say the compound which crystallized, was the bimaleate of compound 27, whose melting point is about 170° C.

EXAMPLES 29 and 30

γ-diethylamino-1-propylamino-5-methyl-(and 5,11-dimethyl)-9-hydroxy-pyrido[4,3-b]carbazoles: compounds 29 and 30, respectively.

To the benzyloxylated compound 24 or 28 (1 mmole) dissolved in 100 ml of ethanol maintained in a water bath heated to 50° to 55° C., was added 40 mg of 30% palladium charcoal and it was stirred under a hydrogen atmosphere at normal pressure for 4 hours. The catalyst was filtered, the solvent evaporated and the residue recrystallized from xylene giving light yellow microcrystals (Table XI).

EXAMPLE 31

The mixture constituted by 1,2-dihydro-1-oxo-5-methyl-9-methoxy pyrido[4,3-b]carbazole 9a (5 g—18 mmoles) and pyridine hydrochloride (50 g) was heated to 220° to 225° C. for 30 minutes and poured into ice water. The precipitate formed was filtered off washed with water and recrystallized from ethanol in the presence of activated charcoal to give 2.6 g (55%) of beige microcrystals, non melting at 350° C.

Analysis: Calculated % for C$_{16}$H$_{12}$N$_2$O$_2$: C, 72.71; H 4.38; N 10.60. Found % C 72.57; H 4.34; N 10.49.

The invention hence provides products of the family of ellipticines bearing various substituents, both on their ring and on their tops 11 and 1. The novel compounds have cytotoxic activities on cell cultures and activity on leukemia which are very pronounced.

The compounds according to the invention also possess a protective power on the viro-induced leukemia of Friend [J. Exp. Med. 1957—105, 307-318]; they are hence also antiviral and antitumoral agents.

Pharmacological tests

The compounds according to the invention tested in the following trials have been used in the form of aqueous solutions prepared in the presence of a sufficient amount of acid to solubilize the compound concerned, unless otherwise stipulated.

Test 1:

Study of the properties of the compounds of the invention on leukemia L1210

A. Measurement of survival time

The following pharmacological trials relate to the effects of the compounds of the invention on leukemia L1210 in vivo.

This inoculated experimental leukemia is in fact known for enabling the selection of active compounds used in human clinics [Zubrod C. G. Proc. Nat. Acad. Sci. 1972, 69, 1042–1047 and Schepartz S., Screening 1971, Cancer Chemother. Part 3; Vol. 2, p. 3].

TABLE XI

Substitution of 1-chloro 5-methyl 9-alkyloxy pyrido [4,3-b]carbazoles 10a–10b–10c–10d Derivatives 11 to 30

| Starting material | Compound obtained | M.P. °C. | Yield % | Reaction condition: time and temperature | Solvent of recrystallization | Empirical formula of the analyzed compound (solvent associated) | Analysis c: calculated % f: found % | | |
|---|---|---|---|---|---|---|---|---|---|
| | | | | | | | C | H | N |
| 10a | 11 | 180–185 | | 2 hours reflux | methanol acetonitrile | $C_{19}H_{20}N_4O$ (½ $H_2O$) | c 69.30 | 6.38 | 17.02 |
| | | | | | | | f 68.88 | 6.29 | 17.13 |
| — | 12 | 190 | 71 | 1 hour reflux | methanol acetonitrile | $C_{20}H_{22}N_4O$ ($CH_2CN$) | c 70.37 | 6.71 | 18.65 |
| | | | | | | | f 70.21 | 6.69 | 18.80 |
| — | 13 | 230–238 (dec) | 48 | 45 minutes reflux | methanol acetonitrile | $C_{21}H_{24}N_4O$(½$CH_3CN$, 1$H_2O$) | c 70.12 | 7.30 | 16.73 |
| | | | | | | | f 69.96 | 6.98 | 16.76 |
| — | 14 | about 115 | 82 | 45 minutes reflux | methanol acetonitrile 1/1 v/v | $C_{22}H_{26}N_4O$(½$CH_3CN$, 3$H_2O$) | c 67.39 | 7.45 | 15.38 |
| | | | | | | | f 67.76 | 7.35 | 15.57 |
| — | 15 | 210–15 | 61.5 | 45 minutes reflux | methanol acetonitrile 1/1 v/v | $C_{23}H_{28}N_4O$ (½ $H_2O$) | c 71.68 | 7.27 | 14.54 |
| | | | | | | | f 71.50 | 7.57 | 14.63 |
| — | 16 | 235–40 | 63 | 19 hours reflux | ethanol acetonitrile 1/1 v/v | $C_{21}H_{24}N_4O$ (½ $H_2O$) | c 70.59 f 70.69 | 7.00 6.87 | 15.68 15.57 |
| — | 17 | 195–200 | 84 | 7 hours reflux | ethanol acetonitrile 1/1 v/v | $C_{22}H_{26}N_4O$ (½ $H_2O$) | c 69.47 | 7.36 | 14.73 |
| | | | | | | | f 69.74 | 7.41 | 13.97 |
| — | 18 | 185–7 | 23 | 2 hours reflux | benzene acetonitrile | $C_{24}H_{30}N_4O$ ($CH_3CN$) | c 72.36 | 7.71 | 16.23 |
| | | | | | | | f 72.72 | 7.73 | 15.80 |
| — | 19 | 74–75 | 40 | 5 hours reflux reflux/$N_2$ in the dark | cyclohexane | $C_{26}H_{34}N_4O$ ($H_2O$) | c 71.52 | 8.31 | 12.83 |
| | | | | | | | f 71.33 | 8.32 | 12.45 |
| — | 20 | 190–5 | 73.5 | 1 hour at 180° C. | xylene | $C_{27}H_{36}N_4O$ (¼ $C_8H_{10}$) | c 71.53 | 7.91 | 17.26 |
| | | | | | | | f 71.55 | 7.92 | 17.43 |
| 10a | 21 | 220 | 64 | 15 hours reflux | ethanol | $C_{22}H_{23}N_3O$ | c 76.49 | 6.71 | 12.17 |
| | | | | | | | f 76.43 | 6.91 | 12.11 |
| 10b | 22 | 228 | 54 | 22 hours reflux | cyclohexane benzene 1/1 v/v | $C_{27}H_{28}N_4O$ | c 76.38 | 6.65 | 13.20 |
| | | | | | | | f 75.67 | 6.62 | 12.70 |
| — | 23 | 230–2 | 45 | 1 hour 20 reflux | xylene | $C_{26}H_{26}N_4O$ (½ $C_2H_5OH$) | c 46.38 | 6.69 | 12.93 |
| | | | | | | | f 75.77 | 6.59 | 12.49 |
| — | 24 | 207–14 | 78.5 | 2 hour 30 reflux | ethanol | $C_{30}H_{34}N_4O$ | c 77.22 | 7.35 | 12.03 |
| | | | | | | | f 76.96 | 7.33 | 11.73 |
| 10c | 25 | 210 | 38 | 30 minutes reflux | benzene | $C_{21}H_{24}N_4O(C_2H_5OH, 2H_2O)$ | c 64.16 | 7.96 | 13.01 |
| | | | | | | | f 63.83 | 7.56 | 12.99 |
| — | 26 | 227 | 51.5 | 6 hours reflux | ethanol | $C_{23}H_{28}N_4O$ ($C_2H_5OH$) | c 71.06 | 8.11 | 13.26 |
| | | | | | | | f 70.85 | 8.21 | 13.11 |
| — | 27 | 156 | 47 | 1 hour reflux | cyclohexane | $C_{25}H_{32}N_4O$ | c 74.22 | 7.97 | 13.85 |
| | | | | | | | f 73.98 | 7.92 | 13.94 |
| 10d | 28 | 175 | 50 | 1 hour 30 reflux | xylene | $C_{31}H_{36}N_4O$ | c 77.45 | 7.55 | 11.66 |
| | | | | | | | f 77.19 | 7.38 | 11.62 |

TABLE XI-continued

Substitution of 1-chloro 5-methyl 9-alkyloxy pyrido [4,3-b]carbazoles 10a–10b–10c–10d Derivatives 11 to 30

| Starting material | Compound obtained | M.P. °C. | Yield % | Reaction condition: time and temperature | Solvent of recrystallization | Empirical formula of the analyzed compound (solvent associated) | Analysis c: calculated % f: found % | | |
|---|---|---|---|---|---|---|---|---|---|
| | | | | | | | C | H | N |
| 24 | 29 | 218–24 | 85 | | xylene | $C_{23}H_{28}N_4O(\frac{1}{2}H_2O)$ | c 71.69 | 7.58 | 14.54 |
| | | | | | | | f 71.97 | 7.55 | 14.26 |
| 28 | 30 | 125 | 62 | | xylene | $C_{24}H_{30}N_4O(H_2O)$ | c 70.56 | 7.90 | 13.72 |
| | | | | | | | f 70.86 | 7.67 | 13.48 |

The properties were determined by the curative action inoculated experimental leukemia L1210. This leukemia was maintained on $B_6D_2Fl$ (C 57 Bl/6×DBA/2) Fl mice in the proportion of 6 or 10 mice per experimental batch. The compounds to be tested were injected by the intraperitoneal route one or several days after inoculation of the cells (1 injection only). The results obtained are collected in Table XII. The death interval was determined, the first figure of the Table indicating the date of the first mouse death and the second the date of the last mouse death. The mean survival time was also measured (MST). A characteristic value is the percentage of increased life span (ILS %). This value (Cancer. Res. 1971, 31, 1883–1887) is the ratio:

$$ILS \% = \frac{S^t - S^c}{S^c} \times 100$$

where
$S^t$ = survival of treated animals and
$S^c$ = survival of control animals.

The results of Table XII show that the products according to the invention possess antileukemia activity.

In the tests reported below, there was selected as a reference compound: 9-methoxy ellipticine used in human clinical medicine in the treatment of acute myeloid leukemias. This compound shows an increase in the life span (ILS) of 26% at the dose closest to the toxic dose, whereas under the same conditions, a compound of the invention, such as compound 27, provides an ILS value of 134%.

B. Effect of the day of inoculation

The experiments were carried out on experimental groups of 6 mice according to the method defined previously by injecting $10^5$ cells on day Do and using the compound 27 according to the invention and varying the day of inoculation of the compound 27 from one group to the next.

TABLE XII

Effect of the compounds of the invention on leukemia L1210 in vivo

| | Compound N° | Dose mg/kg | Day of inoculation | Death interval (mice) | MST | ILS % | Surviving mice |
|---|---|---|---|---|---|---|---|
| $10^5$ cells | Controls | — | — | 9–13 | 10.5 | — | |
| | 9-MeO* | 87.5 | +1 | 13–15 | 13.3 | 26.6 | |
| | 35 | +1 | 11–13 | 11.3 | 7.6 | | |
| | | 17.5 | +1 | 10–13 | 11.2 | 6.6 | |
| $10^5$ cells | Controls | — | — | 10–13 | 11.6 | — | |
| | 9-MeO* | 20 | +2 | 15–21 | 17.6 | 51.7 | |
| | 9-MeO* | 20 | +3 | 18–26 | 20.9 | 80 | |
| $10^5$ cells | 18 | 20 | +3 | 13–19 | 16.1 | 38.8 | — |
| | 19 | 20 | +4 | 11–16 | 12.4 | 19.2 | — |
| | 19 | 10 | +4 | 11–16 | 13 | 25 | — |
| | 29 | 20 | +4 | 10–15 | 12.4 | 19.2 | — |
| | 29 | 10 | +4 | 15–17 | 16.2 | 55.8 | — |
| | 25 | 20 | +4 | 8–12 | 9.6 | — | — |
| | 25 | 10 | +4 | 12–13 | 12.6 | 21.1 | — |
| | 26 | 20 | +4 | 16–19 | 17.4 | 67.3 | — |
| | 26 | 10 | +4 | 12–16 | 14.4 | 38.5 | — |
| | 27 | 20 | +4 | 17–23 | 20.2 | 94.2 | — |
| | 27 | 10 | +4 | 16–27 | 20 | 92.3 | — |
| | 27 | 15 | +1 | 17–43 | 24 | 128.6 | — |
| | 27 | 20 | +3 | 10–30 | 16.5 | 42.7 | — |
| | 27 | 10 | +3 | 12–31 | 17.3 | 49.4 | — |
| ** | 27 | 15 | +1 | 19–35 | 25 | 134 | — |
| ** | 27 | 20 | +1 | 20–31 | 25.5 | 102.4 | 4 |
| ** | 27 | 15 | +1 | 20–32 | 26 | 104.7 | 4 |

*9-methoxy-ellipticine
**Experimental group of six mice

The compound 27 was inoculated at the dose of 15 mg/kg of mouse. As in the above test the death interval was determined, the mean survival time (MST) was measured and the percentage of increased life span (ILS %) was calculated. The results obtained are grouped in Table XIII below.

TABLE XIII

Effect of the day of inoculation of the compound 27

| | Day of inoculation | Death interval | Mean Survival time | ILS % | Surviving mice |
|---|---|---|---|---|---|
| Control | — | 10–14 | 11.5 | 0 | 0 |
| Compound 27 | Do(+3h) | 16–25 | 20.7 | 80 | 0 |
| " | D + 1 | 15–29 | 21 | 82.6 | 2 |
| " | D + 2 | 15–35 | 21.7 | 88.7 | 0 |
| " | D + 3 | 13–25 | 18 | 56.5 | 0 |
| " | D + 4 | 14–20 | 16 | 39.1 | 0 |

The above results show that compound 27 is more active one day after inoculation of the cells (2 surviving mice in 6 treated mice); this means that the compound 27 is more active with respect to the cells in division. On day D+2 the compound 27 still had a strong activity (ILS % = 88.7) whereas the number of cells has considerably increased, which explains the apparent drop in activity of the compound 27 on days D+3 and D+4 which is due to the increasing number of tumoral cells in the peritoneum of the animal.

C. Dose/Effect relationship

The study was carried out on experimental groups of six mice by the previously defined method. $10^5$ cells were injected at day Do. The injection was carried out on day D+1 with compound 27 at doses of 5 mg/kg; 10 mg/kg; 15 mg/kg and 20 mg/kg. The death interval was determined, the mean survival time was measured (MST) and the percentage of increased life span was calculated (ILS %) by the above-defined formula. The results obtained are reported in Table XIV below.

TABLE XIV

Dose/effect relationship

| | Dose mg/kg | Death Interval | Mean Survival time | ILS % | Surviving mice |
|---|---|---|---|---|---|
| Control | — | 10–12 | 10.7 | — | 0 |
| Compound 27 | 5 | 16–24 | 19.3 | 80.4 | 0 |
| " | 10 | 14–21 | 16.8 | 57 | 0 |
| " | 15 | 13–31 | 21 | 96.3 | 0 |
| " | 20 | 15–25 | 18.8 | 75.7 | 1 |

The results of Table XIV show that the activity of the compound 27 is proportional to the dose inoculated. If the ILS calculated for the dose of 20 mg/kg seems less than that obtained at the dose 15 mg/kg it is because in the calculation the finally cured mice do not enter.

Test 2

"In vitro" cytotoxic study of the compounds of the invention on the cells of viro-induced leukemia of Friend in the mouse [J. Exp. Med. 1957, 105, p. 307–318].

The cells were grown in suspension in the RPMI 1640 medium [catalogue of GIBCO Bio-Cult-Ltd, Washington Road Sandyford Industrial Estate Paisley PA3 4EP Renfrewshire Scotland] supplement with 20% of embryonary calf serum, with penicillin and with streptopycin. The duplication time of the culture was about 11 hours. The growth factor is equal to 1 or very close to 1 (all the cells multiplying).

The cultures were seeded at times t=0 at the concentration of $2 \times 10^5$ cells per ml in Falcon dishes containing 4 ml of medium. 24 hours later, the product to be tested (in solution, in acetic water) was added, at the moment when the cells were in the exponential growth phase. 24 hours after the addition of the product, the cells were counted and the percentage of living cells determined by an exclusion test with trypan blue.

Two doses could be defined:
(1) the 100% lethal dose (LD 100)
(2) the 50% lethal dose (LD 50)
The results are indicated in Table XV.

TABLE XV

"In vitro" cytotoxic study of the compounds of the invention on cells of the Friend leukemia of the mouse

| | LD 100 (molar conc.) | LD 50 | LD 50 HUM / LD 50 product |
|---|---|---|---|
| Reference product: 9-hydroxy ellipticinium aceto methylate | $8 \cdot 10^{-7}$ | $3 \cdot 10^{-7}$ | 1 |

TABLE XV-continued

"In vitro" cytotoxic study of the compounds of the invention on cells of the Friend leukemia of the mouse

| | LD 100 (molar conc.) | LD 50 | LD 50 HUM / LD 50 product |
|---|---|---|---|
| (HUM) Compounds of the invention | | | |
| 11 | $2.5 \cdot 10^{-7}$ | $10^{-7}$ | 3 |
| 12 | $7 \cdot 10^{-7}$ | $2.5 \cdot 10^{-7}$ | 1.5 |
| 13 | $1.5 \cdot 10^{-5}$ | $7 \cdot 10^{-6}$ | 0.04 |
| 14 | $1.5 \cdot 10^{-6}$ | $5 \cdot 10^{-7}$ | 0.6 |
| 15 | $2 \cdot 10^{-6}$ | $8 \cdot 10^{-7}$ | 0.4 |
| 16 | $3 \cdot 10^{-6}$ | $8 \cdot 10^{-7}$ | 0.4 |
| 17 | $3 \cdot 10^{-6}$ | $1.5 \cdot 10^{-6}$ | 0.2 |
| 18 | $1.5 \cdot 10^{-6}$ | $5 \cdot 10^{-7}$ | 0.6 |
| 19 | $3 \cdot 10^{-6}$ | $1.3 \cdot 10^{-6}$ | 0.2 |
| 21 | $10^{-4}$ | $3.5 \cdot 10^{-5}$ | 1.1 |
| 23 | $9 \cdot 10^{-7}$ | $3 \cdot 10^{-7}$ | 1 |
| 24 | $10^{-5}$ | $3 \cdot 10^{-6}$ | 0.1 |
| 25 | $3 \cdot 10^{-7}$ | $1.2 \cdot 10^{-7}$ | 3 |
| 26 | $10^{-6}$ | $4 \cdot 10^{-7}$ | 0.75 |
| 27 | $1.2 \cdot 10^{-6}$ | $4.5 \cdot 10^{-7}$ | 0.65 |
| 29 | $4 \cdot 10^{-8}$ | $1.7 \cdot 10^{-8}$ | 18 |

These results show that the majority of products are cytotoxic at concentrations comprised between $3 \cdot 10^{-6}$ and $3 \cdot 10^{-7}$ M.

Three compounds (compounds 11, 25 and 29) are more active than the derivatives already known, in particular 2-methyl-9-hydroxy ellipticinium acetate used as a reference product (HUM). The other compounds are practically as active as HUM.

Test 3

Cytotoxic "in vitro" study on hamster cells on leukemia L1210 cells of the serie.

In particular, the line BHK 21 of hamster cells and a clone derived from this line were used, converted by the virus of the hamster sarcoma (clone HS5).

After detachment by trypsin, the cells were placed under culture in plastic Petri dishes of 35 mm diameter at the concentration of $2 \cdot 10^5$ cells/dish, in a "Eagle" culture medium supplemented with "Bactotryptophosphate Broth Difco" and with 10% of calf serum [M. STOKER and I. MAC-PHERSON Virology, 14, 1961, 359].

After 5 hours, the cells were attached to a plastic support and the products to be tested whose solutions had been formed in water or in DMSO (dimethylsulphoxide) if the product was little soluble in water, was added. In the latter case a control was carried out with the same final concentration of DMSO in the culture medium.

The state of the cells was examined 24, 48 and 72 hours later.

In the case of the L1210 cells, the tests were carried out in a medium gelled with agarose, the L1210 cells growing in suspension.

The results are indicated in Table XVI.

The results (Table XVI) show clearly that the products, with the exception of the product 21, are distinctly cytotoxic at concentrations comprised between 0.4 and 5 μM, and that the most active products, that is to say the compounds 24 and 27, are almost as active as the reference dipyrido-indole (BD40).

The inhibitive effects on the two types of cells, normal and transformed, are similar.

TABLE XVI

| | 11 | 12 | 13 | 14 | 15 | 16 | 17 | 18 | 21 | 24 | 25 | 27 | Reference≠ BD 40 |
|---|---|---|---|---|---|---|---|---|---|---|---|---|---|
| C13/8 | 1μM | 2 | 2 | 2 | 2 | 1 | 1 | 5 | >5 | | | | 0.25 |
| HS5 | 1 | 2 | 2 | 2 | 2 | 2 | 2 | 5 | >5 | | | | 0.25 |
| L1210 | | | | | | | | | | 0.4 | 0.9 | 0.6 | 0.2 |

Minimal dose leading to a complete inhibition of the growth

≠BD 40 = 1-γ-diethylaminopropyl)-amino-5-methyl-dipyrido[4,3-b][3,4-f]indole.

It is noted that compound 21 does not come within the scope of the general formula of the claimed compounds.

Test 4

Viro-induced leukemia: Friends leukemia.

The following experiments related to the treatment of mice inoculated by the virus of Friend's leukemia.

In these experiments DBA$_2$, male mice, aged from 2 to 3 months, of weight around 20 g, were used.

An anemia inducing strain of Friend's virus (VFA) maintained for several years in the laboratory was used. The viral stock was constituted by an acellular supernatant liquor obtained by the centrifugation of a ground product of leukemic spleens, carried out in an 0.5 M PBS-saccharose solution. The assay of the stock was done in vivo by the method described by JASMIN et al [J. Nat. Cancer Inst. 1974,53, 469-474]. The measurement is expressed in SD$_{50}$ (50% spleen enlarging dose).

A. Measurement of splenomegaly

1. Test procedure

The Friend virus was injected in the mouse by the intraperitoneal route. The animal then developed a characteristic splenomegaly. The mortality appearing about 3 weeks after the viral inoculation at the doses of virus normally employed, the animals were sacrificed on day +15 after infection, for study of the splenomegaly. The spleens were removed and then weighed individually. Each mouse whose spleen had a weight higher than 250 mg was considered as leukemic.

2. Results

The results obtained are assembled in the Table XVII below. They show that compound 27 according to the invention has a protective power on Friend's leukemia.

TABLE XVII

Friend's Leukemia (measurement of splenomegaly)

| Virus inoculated at day 0 | Dilution of the virus | Compound tested | Dose | Day of injection | Mean weight of the spleen (mg)** | Number of mice inoculated | Number of leukemic mice |
|---|---|---|---|---|---|---|---|
| VFA | 1/800 | PBS*** | 0.1 ml/ mouse | D + 1 | 1,503 (2,074–1,055) | 10 | 10/10 |
| VFA | 1/800 | Compound 27 | 0.2 mg/ mouse 10 mg/kg | D + 1 | 183 (269–123) | 10 | 2/10 |
| VFA | 1/1600 | PBS*** | 0.1 ml/ mouse | D + 1 | 827 (1,977–158) | 10 | 7/10 |
| VFA | 1/1600 | Compound 27 | 0.2 mg/ mouse 10 mg/kg | D + 1 | 199 (236–155) | 5 | 0/5 |
| VFA | 1/3200 | PBS*** | 0.1 ml/ mouse | D + 1 | 477 (1,117–100) | 10 | 7/10 |
| VFA | 1/3200 | Compound 27 | 0.2 mg/ mouse 10 mg/kg | D + 1 | 220 (280–191) | 5 | 1/5 |

*The mice whose spleen weight was higher than 250 mg were considered as leukemic.
**In parentheses, the spleen with the highest weight (first figure) and that with the lowest weight (second figure).
***Phosphate buffer.

B. Measurement of survival time

In another series of tests, the mortality of the mice, in which the Friend's virus was injected (VFA) by the intraperitoneal route (dilution 1/800) and the death intervalwere determined, the mean survival time and the percentage of increased life span for the compound 27 according to the invention inoculated on day D+1 at the dose of 15 mg/kg were calculated.

The results obtained are grouped in Table XVIII below.

TABLE XVIII

Test on anemia inducing Friend's virus

| Dilution of the VFA virus | Compound tested | Death interval | Mean survival time | ILS % | Survive |
|---|---|---|---|---|---|
| 1/800 % of leukemias = 99.8 | Virus Control 1 | 19–43 | 30.5 ⎫ 30.15 | — | 1 |
| | Virus Control 2 | 22–37 | 29.8 ⎭ | — | 0 |
| | Compound 27* 15 mg/kg | 20–64 | 42.2 | 40 | 0 |
| 1/800 % of leukemias = 100% | Virus Control 1 | 19–46 | 24.4 | | |
| | Virus Control 2 | 19–35 | 24.4 | | |
| | Compound 27** 15 mg/kg | 48–72 | 59.5 | 143.85 | — |

*group of 10 mice - at this dose 45 mice/10 died through toxicity; the calculation of the ILS % was carried out on the surviving mice.
**group of 10 mice.

C. Dose/effect relationship

Experimental groups of 10 mice were used, into which the VFA virus (dilution 1/800—% of leukemias=100%) was injected on day Do. The compound 27 according to the invention was then injected at day D+1 at various doses according to the groups and the death interval, the mean survival time and the percentage of increased life span were determined.

The results obtained are grouped in Table XIX below. These results show that the activity of compound 27 is proportional to the inoculated dose.

The novel compounds can be administered to man and to mammals by the usual means. A suitable method of administration is the intravenous or intramuscular injectable route. The intravenous route is preferred.

Thus the invention relates also to the pharmaceutical compositions suitable for the administration and containing at least one compound of the invention in association with a pharmaceutical acceptable vehicle. For example, a pharmaceutical composition suitable for the needs of the invention is an injectable solution prepared from a pharmaceutically acceptable salt of a derivative according to the invention or prepared extemporaneously from a derivative according to the invention with suitable amounts of an acid to obtain a solution having a pH close to 7. Such a solution could contain customary additives in a pharmaceutical formulation, for example buffering agents.

In the course of the pharmacological tests, no immediate notable side effect was found. The LD 50 values characteristic of the toxicity of the medicaments are those determined for a large number of representative compounds according to the invention.

As for the posology envisaged, it will obviously depend on the particular compound used and the disease to be treated. In man, doses of about 100 mg of more of the active compound can be suitable for the adult.

TABLE XIX

D - Test on the anemia inducing Friend's virus: dose/effect relationship

| Compound tested | Death interval | Mean survival time | ILS % | Surviving mice |
|---|---|---|---|---|
| Virus Control 1 | 18-31 | 24.4 ⎫ 23.6 | — | 0 |
| Virus Control 2 | 18-29 | 22.8 ⎭ | | |
| Compound 27 5 mg/kg | 25-36 | 31.1 | 31.78 | 0 |
| Compound 27 10 mg/kg | 32-64 | 45.8 | 103 | 0 |
| Compound 27 15 mg/kg* | 33-63 | 49.9 | 122 | 0 |

*Two deaths through toxicity; they do not enter into the calculation.

We claim:

1. A compound of the formula

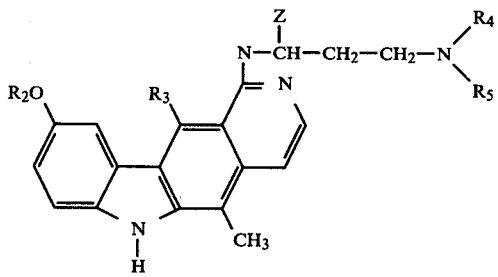

wherein Z, $R_2$ and $R_3$ are selected from the group consisting of hydrogen and methyl, $R_4$ and $R_5$ are selected from the group consisting of hydrogen, methyl and ethyl, and their non-toxic, pharmaceutically acceptable acid addition salts.

2. A compound of claim 1 wherein Z is hydrogen and $R_2$ and $R_3$ are methyl.

3. A compound of claim 1 wherein Z is hydrogen, $R_4$ and $R_5$ are ethyl, $R_2$ is hydrogen and $R_3$ is methyl.

* * * * *

UNITED STATES PATENT AND TRADEMARK OFFICE
CERTIFICATE OF CORRECTION

PATENT NO. : 4,434,290
DATED : February 28, 1984
INVENTOR(S) : EMILE BISAGNI ET AL.

Page 1 of 3

It is certified that error appears in the above—identified patent and that said Letters Patent is hereby corrected as shown below:

Column 3, line 67: "an other" should read -- another --.
Column 5, structural formula in "Fifth Step",
        "$R_3O$" should read -- $R_2O$ --.
Column 6, structural formula in "Sixth Step",
        "$R_3O$" should read -- $R_2O$ --.
Column 10, line 62: "60 g" should read -- 69 g --.
Column 12, before "EXAMPLE 3", please insert
        -- IR : $\nu$ NH : 3220 to 3260,
        $\nu C = 0$ : 1630 to 1640 $cm^{-1}$. --
Columns 19 and 20, the Analysis for Compound 16 should read:
        -- c   70.59   7.00   15.68
           f   70.69   6.87   15.57 --,
after the Empirical Formula for Compound 16,
        delete "f 70.69",
the Empirical formula for Compound 17
        "$C_{22}H_{26}N_4O$ (½ $H_2O$)" should read
   -- $C_{22}H_{26}N_4O$ ($H_2O$) --,
in the Analysis N column for Compound 20,
        "17.43" should read -- 17.46 --,
in the Analysis C column for Compound 23,
        "C 46.38" should read -- 74.82 --,

UNITED STATES PATENT AND TRADEMARK OFFICE
CERTIFICATE OF CORRECTION

PATENT NO. : 4,434,290
DATED : February 28, 1984
INVENTOR(S) : EMILE BISAGNI ET AL.

It is certified that error appears in the above—identified patent and that said Letters Patent is hereby corrected as shown below:

Column 19 and 20, in the Analysis N column for compound 24,
"12.03" should read -- 12.01 --,
in the Analysis C column for compound 28,
"77.45" should read -- 77.46 --.

Column 21, correct this portion of Table XII to read:

--

Effect of the compounds of the invention on leukemia L 1210 in vivo

|  | Compound No. | Dose mg/kg | Day of inoculation | Death interval (mice) | MST | ILS% | Surviving mice |
|---|---|---|---|---|---|---|---|
| $10^5$ cells | Controls | - | - | 9-13 | 10.5 | - |  |
|  | 9-MeO* | 87.5 | + 1 | 13-15 | 13.3 | 26.6 |  |
|  |  | 35 | + 1 | 11-13 | 11.3 | 7.6 |  |
|  |  | 17.5 | + 1 | 10-13 | 11.2 | 6.6 |  |
| $10^4$ cells | Controls | - | - | 10-13 | 11.6 | - |  |
|  | 9-MeO* | 20 | + 2 | 15-21 | 17.6 | 51.7 |  |

--

UNITED STATES PATENT AND TRADEMARK OFFICE
CERTIFICATE OF CORRECTION

PATENT NO. : 4,434,290

DATED : February 28, 1984  Page 3 of 3

INVENTOR(S) : EMILE BISAGNI ET AL.

It is certified that error appears in the above—identified patent and that said Letters Patent is hereby corrected as shown below:

Column 23, line 41: "supplement" should read
-- supplemented --.

Signed and Sealed this

Fourth Day of December 1984

[SEAL]

Attest:

GERALD J. MOSSINGHOFF

*Attesting Officer*  *Commissioner of Patents and Trademarks*